(12) United States Patent
Blair

(10) Patent No.: US 8,358,212 B2
(45) Date of Patent: Jan. 22, 2013

(54) MULTI-MODAL TRANSPONDER AND METHOD AND APPARATUS TO DETECT SAME

(75) Inventor: William A. Blair, San Diego, CA (US)

(73) Assignee: RF Surgical Systems, Inc., Bellevue, WA (US)

(*) Notice: Subject to any disclaimer, the term of this patent is extended or adjusted under 35 U.S.C. 154(b) by 787 days.

(21) Appl. No.: 12/472,199

(22) Filed: May 26, 2009

(65) Prior Publication Data

US 2009/0315681 A1 Dec. 24, 2009

Related U.S. Application Data

(60) Provisional application No. 61/056,229, filed on May 27, 2008, provisional application No. 61/102,749, filed on Oct. 3, 2008.

(51) Int. Cl.
*G08B 21/00* (2006.01)
(52) U.S. Cl. ............... 340/572.7; 340/572.1; 340/572.5; 340/10.1; 455/1; 342/44
(58) Field of Classification Search .............. 340/572, 340/10; 455/1; 342/44
See application file for complete search history.

(56) References Cited

U.S. PATENT DOCUMENTS

| | | | |
|---|---|---|---|
| 2,740,405 A | 4/1956 | Riordan | |
| 3,031,864 A | 5/1962 | Freundlich | |
| 3,422,816 A | 1/1969 | Robinson et al. | |
| 3,587,583 A | 6/1971 | Greenberg | |
| D240,166 S | 6/1976 | Cartmell et al. | |
| 4,034,297 A | 7/1977 | Giorgi et al. | |
| 4,114,601 A | 9/1978 | Abels | |
| 4,193,405 A | 3/1980 | Abels | |
| D272,943 S | 3/1984 | Stone et al. | |
| 4,477,256 A | 10/1984 | Hirsch | |
| 4,540,398 A | 9/1985 | Barson et al. | |
| 4,626,251 A | 12/1986 | Shen | |
| 4,636,208 A | 1/1987 | Rath | |

(Continued)

FOREIGN PATENT DOCUMENTS

| AU | 199852698 B2 | 3/1993 |
|---|---|---|
| AU | 2003249257 A1 | 2/2004 |

(Continued)

OTHER PUBLICATIONS

Barnes et al., "Design for a FET based 1 MHz, 10kV Pulse Generator," Pulsed Power Conference, Digest of Technical Papers, Tenth IEEE International, 2:1335-1340, 1995.

(Continued)

*Primary Examiner* — Jennifer Mehmood
*Assistant Examiner* — Mark Rushing
(74) *Attorney, Agent, or Firm* — Seed IP Law Group PLLC

(57) ABSTRACT

An integral detection and identification system for detecting and identifying an object includes an identification transponder and a presence/absence transponder. The identification transponder includes a first inductive winding wound about a core and electrically coupled to an integrated circuit to transmit an identification signal in response to receipt of an interrogation signal in a first frequency range. The identification signal encodes an identifier stored by the integrated circuit. The presence/absence transponder includes a resonant inductive/capacitive tank circuit having at least a second inductive winding wound about a core and electrically coupled to a capacitor to transmit a presence/absence signal in response to an interrogation signal in a second frequency range. The presence/absence response signal lacks unique identifying information and is physically coupled to the identification transponder to form an integral detection and identification transponder that can selectively be attached to the object.

17 Claims, 8 Drawing Sheets

U.S. PATENT DOCUMENTS

| | | | |
|---|---|---|---|
| 4,639,253 A | 1/1987 | Dyer et al. |
| 4,645,499 A | 2/1987 | Rupinskas |
| 4,658,818 A | 4/1987 | Miller, Jr. et al. |
| 4,681,111 A | 7/1987 | Silvian |
| 4,704,109 A | 11/1987 | Rupinskas |
| 4,718,897 A | 1/1988 | Elves |
| 4,893,118 A | 1/1990 | Lewiner et al. |
| 4,917,694 A | 4/1990 | Jessup |
| 4,935,019 A | 6/1990 | Papp, Jr. |
| 4,938,901 A | 7/1990 | Groitzsch et al. |
| 4,992,675 A | 2/1991 | Conner, Jr. et al. |
| 5,041,103 A | 8/1991 | Rupinskas |
| 5,045,080 A | 9/1991 | Dyer et al. |
| 5,049,219 A | 9/1991 | Johns et al. |
| 5,057,095 A | 10/1991 | Fabian |
| 5,105,829 A | 4/1992 | Fabian et al. |
| 5,107,862 A | 4/1992 | Fabian et al. |
| 5,112,325 A | 5/1992 | Zachry |
| D330,872 S | 11/1992 | Ball |
| 5,181,021 A | 1/1993 | Lee et al. |
| 5,188,126 A | 2/1993 | Fabian et al. |
| 5,190,059 A | 3/1993 | Fabian et al. |
| 5,224,593 A | 7/1993 | Bennett |
| 5,235,326 A | 8/1993 | Beigel et al. |
| 5,258,742 A | 11/1993 | Soldevila Domingo et al. |
| 5,329,944 A | 7/1994 | Fabian et al. |
| 5,353,011 A | 10/1994 | Wheeler et al. |
| D353,343 S | 12/1994 | Eberhardt |
| D354,927 S | 1/1995 | Andrau |
| D356,052 S | 3/1995 | Andrau |
| D359,705 S | 6/1995 | Ball |
| 5,446,447 A | 8/1995 | Carney et al. |
| 5,450,622 A | 9/1995 | Vandegraaf |
| 5,456,718 A | 10/1995 | Szymaitis |
| 5,482,036 A | 1/1996 | Diab et al. |
| 5,557,279 A * | 9/1996 | D'Hont ............................ 342/42 |
| 5,575,781 A | 11/1996 | DeBusk |
| D378,614 S | 3/1997 | Jensen |
| 5,650,596 A | 7/1997 | Morris et al. |
| 5,664,582 A | 9/1997 | Szymaitis |
| D385,037 S | 10/1997 | Jensen |
| 5,725,517 A | 3/1998 | DeBusk |
| 5,792,128 A | 8/1998 | DeBusk |
| D412,135 S | 7/1999 | Saito |
| 5,923,001 A | 7/1999 | Morris et al. |
| 5,928,151 A | 7/1999 | Hossack et al. |
| 5,931,824 A | 8/1999 | Stewart et al. |
| 5,963,132 A | 10/1999 | Yoakum |
| 5,969,613 A | 10/1999 | Yeager et al. |
| D418,773 S | 1/2000 | Saito |
| 6,026,818 A | 2/2000 | Blair et al. |
| D423,673 S | 4/2000 | Bassøe |
| 6,075,797 A | 6/2000 | Thomas |
| 6,093,869 A | 7/2000 | Roe et al. |
| D429,337 S | 8/2000 | Sanfilippo |
| 6,172,608 B1 | 1/2001 | Cole |
| 6,201,469 B1 | 3/2001 | Balch et al. |
| 6,211,666 B1 | 4/2001 | Acker |
| 6,215,437 B1 | 4/2001 | Schürmann et al. |
| 6,223,137 B1 | 4/2001 | McCay et al. |
| 6,232,878 B1 | 5/2001 | Rubin |
| 6,276,033 B1 | 8/2001 | Johnson et al. |
| 6,317,027 B1 | 11/2001 | Watkins |
| 6,349,234 B2 | 2/2002 | Pauly et al. |
| 6,353,406 B1 | 3/2002 | Lanzl et al. |
| 6,359,562 B2 | 3/2002 | Rubin |
| 6,366,206 B1 | 4/2002 | Ishikawa et al. |
| D456,907 S | 5/2002 | Sanfilippo |
| D457,634 S | 5/2002 | Rouns et al. |
| 6,384,296 B1 | 5/2002 | Roe et al. |
| 6,401,722 B1 | 6/2002 | Krag |
| 6,441,741 B1 | 8/2002 | Yoakum |
| D471,281 S | 3/2003 | Baura et al. |
| 6,557,752 B1 | 5/2003 | Yacoob |
| 6,566,997 B1 | 5/2003 | Bradin |
| 6,588,661 B2 | 7/2003 | Degrauwe et al. |
| 6,632,216 B2 | 10/2003 | Houzego et al. |
| 6,633,226 B1 | 10/2003 | Nysen |
| 6,641,039 B2 | 11/2003 | Southard |
| 6,648,223 B2 | 11/2003 | Boukhny et al. |
| 6,650,240 B2 | 11/2003 | Lee et al. |
| 6,654,629 B2 | 11/2003 | Montegrande |
| 6,696,954 B2 | 2/2004 | Chung |
| 6,734,795 B2 | 5/2004 | Price |
| 6,753,783 B2 | 6/2004 | Friedman et al. |
| D495,055 S | 8/2004 | Silber |
| 6,774,800 B2 | 8/2004 | Friedman et al. |
| 6,777,623 B2 | 8/2004 | Ballard |
| 6,778,089 B2 | 8/2004 | Yoakum |
| 6,786,405 B2 | 9/2004 | Wiedenhoefer |
| 6,812,824 B1 | 11/2004 | Goldinger et al. |
| 6,812,842 B2 | 11/2004 | Dimmer |
| 6,822,570 B2 | 11/2004 | Dimmer et al. |
| 6,832,398 B2 | 12/2004 | Borders et al. |
| 6,838,990 B2 | 1/2005 | Dimmer |
| D502,419 S | 3/2005 | Copen |
| 6,861,639 B2 | 3/2005 | Al-Ali |
| 6,861,954 B2 | 3/2005 | Levin |
| 6,879,300 B2 | 4/2005 | Rochelle et al. |
| 6,909,366 B1 | 6/2005 | Marsh et al. |
| D511,004 S | 10/2005 | Masuda |
| D511,384 S | 11/2005 | Masuda |
| 6,977,504 B2 | 12/2005 | Wright et al. |
| 6,998,541 B2 | 2/2006 | Morris et al. |
| 7,001,366 B2 | 2/2006 | Ballard |
| 7,019,650 B2 | 3/2006 | Volpi et al. |
| 7,026,924 B2 | 4/2006 | Degrauwe et al. |
| 7,026,927 B2 | 4/2006 | Wright et al. |
| 7,037,336 B2 | 5/2006 | Ward |
| D526,586 S | 8/2006 | McCaghren et al. |
| 7,098,793 B2 | 8/2006 | Chung |
| 7,118,029 B2 | 10/2006 | Nycz et al. |
| 7,135,973 B2 | 11/2006 | Kittel et al. |
| 7,135,978 B2 | 11/2006 | Gisselberg et al. |
| 7,142,118 B2 | 11/2006 | Hamilton et al. |
| 7,142,815 B2 | 11/2006 | Desjeux et al. |
| D534,448 S | 1/2007 | Shaffer, II et al. |
| 7,158,030 B2 | 1/2007 | Chung |
| 7,158,754 B2 | 1/2007 | Anderson |
| 7,160,258 B2 | 1/2007 | Imran et al. |
| D536,673 S | 2/2007 | Silber |
| 7,176,798 B2 | 2/2007 | Dimmer et al. |
| 7,183,914 B2 | 2/2007 | Norman et al. |
| 7,183,927 B2 | 2/2007 | Kolton et al. |
| 7,245,893 B1 | 7/2007 | Husted et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,299,981 B2 | 11/2007 | Hickle et al. |
| D557,423 S | 12/2007 | Chen |
| D558,352 S | 12/2007 | Sanfilippo |
| 7,307,530 B2 | 12/2007 | Fabian et al. |
| D558,882 S | 1/2008 | Brady |
| 7,319,396 B2 | 1/2008 | Homanfar et al. |
| 7,319,397 B2 | 1/2008 | Chung et al. |
| 7,325,723 B2 | 2/2008 | Desjeux |
| 7,333,013 B2 | 2/2008 | Berger |
| 7,342,497 B2 | 3/2008 | Chung et al. |
| 7,362,228 B2 | 4/2008 | Nycz et al. |
| D568,186 S | 5/2008 | Blair et al. |
| 7,382,255 B2 | 6/2008 | Chung |
| 7,397,364 B2 | 7/2008 | Govari |
| 7,399,899 B2 | 7/2008 | Fabian |
| 7,408,168 B1 | 8/2008 | Aufrichtig et al. |
| 7,420,468 B2 | 9/2008 | Fabian et al. |
| 7,423,535 B2 | 9/2008 | Chung et al. |
| 7,446,646 B2 | 11/2008 | Huomo |
| 7,449,614 B2 | 11/2008 | Ales, III |
| 7,464,713 B2 | 12/2008 | Fabian et al. |
| 7,465,847 B2 | 12/2008 | Fabian |
| D584,414 S | 1/2009 | Lash et al. |
| 7,474,222 B2 | 1/2009 | Yang et al. |
| 7,492,257 B2 | 2/2009 | Tethrake et al. |
| 7,492,263 B2 | 2/2009 | Marsilio et al. |
| 7,508,308 B2 | 3/2009 | Chung |
| D590,342 S | 4/2009 | Dávila et al. |
| 7,513,425 B2 | 4/2009 | Chung |

| | | | |
|---|---|---|---|
| D598,110 S | 8/2009 | Phillips et al. | |
| D598,114 S | 8/2009 | Cryan | |
| 7,696,877 B2 | 4/2010 | Barnes et al. | |
| 7,769,422 B2 | 8/2010 | DiSilvestro et al. | |
| 7,855,656 B2 | 12/2010 | Maschke | |
| 7,876,097 B2 | 1/2011 | Greim | |
| 7,898,420 B2 | 3/2011 | Blair et al. | |
| 8,111,162 B2 | 2/2012 | Barnes et al. | |
| 2001/0030610 A1 | 10/2001 | Rochelle et al. | |
| 2002/0011932 A1 | 1/2002 | Rodgers et al. | |
| 2002/0032435 A1 | 3/2002 | Levin | |
| 2002/0070863 A1 | 6/2002 | Brooking | |
| 2002/0143320 A1 | 10/2002 | Levin | |
| 2002/0165587 A1 | 11/2002 | Zhang et al. | |
| 2002/0188259 A1 | 12/2002 | Hickle et al. | |
| 2003/0004411 A1 | 1/2003 | Govari et al. | |
| 2003/0052788 A1 | 3/2003 | Kwong-Tai Chung | |
| 2003/0105394 A1 | 6/2003 | Fabian et al. | |
| 2003/0111592 A1 | 6/2003 | Al-Ali | |
| 2004/0008123 A1 | 1/2004 | Carrender et al. | |
| 2004/0129279 A1 | 7/2004 | Fabian et al. | |
| 2004/0137844 A1 | 7/2004 | Desjeux et al. | |
| 2004/0138554 A1 | 7/2004 | Dimmer et al. | |
| 2004/0250819 A1 | 12/2004 | Blair et al. | |
| 2004/0254420 A1 | 12/2004 | Ward | |
| 2005/0049564 A1 | 3/2005 | Fabian | |
| 2005/0110640 A1 | 5/2005 | Chung | |
| 2005/0131397 A1 | 6/2005 | Levin | |
| 2005/0154293 A1 | 7/2005 | Gisselberg et al. | |
| 2005/0212673 A1* | 9/2005 | Forster | 340/572.7 |
| 2005/0247794 A1 | 11/2005 | Jones et al. | |
| 2005/0249036 A1 | 11/2005 | Davies et al. | |
| 2005/0267550 A1 | 12/2005 | Hess et al. | |
| 2006/0055537 A1* | 3/2006 | Jackson | 340/572.1 |
| 2006/0084934 A1 | 4/2006 | Frank | |
| 2006/0106368 A1 | 5/2006 | Miller et al. | |
| 2006/0109086 A1* | 5/2006 | Amtmann | 340/10.3 |
| 2006/0187044 A1* | 8/2006 | Fabian et al. | 340/572.1 |
| 2006/0194899 A1 | 8/2006 | Ohashi et al. | |
| 2006/0202827 A1 | 9/2006 | Volpi et al. | |
| 2006/0232407 A1 | 10/2006 | Ballard | |
| 2006/0235488 A1 | 10/2006 | Nycz et al. | |
| 2006/0241396 A1 | 10/2006 | Fabian et al. | |
| 2006/0241399 A1 | 10/2006 | Fabian | |
| 2006/0244597 A1 | 11/2006 | Tethrake et al. | |
| 2006/0244652 A1 | 11/2006 | Tethrake et al. | |
| 2006/0270933 A1 | 11/2006 | Benson et al. | |
| 2007/0004994 A1 | 1/2007 | Sherman | |
| 2007/0005141 A1 | 1/2007 | Sherman | |
| 2007/0034670 A1 | 2/2007 | Racenet et al. | |
| 2007/0038233 A1 | 2/2007 | Martinez et al. | |
| 2007/0055109 A1 | 3/2007 | Bass et al. | |
| 2007/0109099 A1 | 5/2007 | Raphaeli et al. | |
| 2007/0125392 A1 | 6/2007 | Olson, Jr. et al. | |
| 2007/0152823 A1* | 7/2007 | Hirahara et al. | 340/572.1 |
| 2007/0209957 A1 | 9/2007 | Glenn et al. | |
| 2007/0216062 A1 | 9/2007 | Frank | |
| 2007/0219516 A1 | 9/2007 | Patel et al. | |
| 2007/0238982 A1 | 10/2007 | Caylor, III | |
| 2007/0239289 A1 | 10/2007 | Cambre et al. | |
| 2007/0244470 A1 | 10/2007 | Barker, Jr. et al. | |
| 2007/0265690 A1 | 11/2007 | Lichtenstein et al. | |
| 2007/0270660 A1 | 11/2007 | Caylor, III et al. | |
| 2007/0285249 A1 | 12/2007 | Blair et al. | |
| 2008/0007411 A1 | 1/2008 | Levin | |
| 2008/0021308 A1 | 1/2008 | Dimmer et al. | |
| 2008/0030303 A1 | 2/2008 | Kobren et al. | |
| 2008/0051746 A1 | 2/2008 | Shen-Gunther | |
| 2008/0058637 A1 | 3/2008 | Fischell et al. | |
| 2008/0126122 A1 | 5/2008 | Warner et al. | |
| 2008/0132860 A1 | 6/2008 | Smith et al. | |
| 2008/0204245 A1 | 8/2008 | Blair et al. | |
| 2008/0231452 A1 | 9/2008 | Levin | |
| 2008/0237341 A1 | 10/2008 | Fleck et al. | |
| 2008/0238677 A1 | 10/2008 | Blair et al. | |
| 2008/0243404 A1 | 10/2008 | Banhegyesi | |
| 2008/0272913 A1 | 11/2008 | Barnes et al. | |
| 2008/0281190 A1 | 11/2008 | Petcavich et al. | |
| 2008/0296373 A1 | 12/2008 | Zmood et al. | |
| 2009/0014518 A1 | 1/2009 | Stewart et al. | |
| 2010/0033309 A1 | 2/2010 | Blair | |
| 2010/0108079 A1 | 5/2010 | Blair | |
| 2010/0109848 A1 | 5/2010 | Blair et al. | |
| 2011/0004276 A1 | 1/2011 | Blair et al. | |
| 2011/0181394 A1 | 7/2011 | Blair | |

FOREIGN PATENT DOCUMENTS

| | | | |
|---|---|---|---|
| CN | 1014600096 A | 6/2009 | |
| EP | 1 612 554 A1 | 1/2006 | |
| EP | 2 087 850 A2 | 8/2009 | |
| JP | 2009539478 A | 11/2009 | |
| WO | 02/39917 A1 | 5/2002 | |
| WO | 2004/008387 A1 | 1/2004 | |
| WO | 2004/086997 A1 | 10/2004 | |
| WO | 2006/060781 A1 | 6/2006 | |
| WO | 2007/146091 A1 | 12/2007 | |
| WO | 2008/024921 A1 | 2/2008 | |
| WO | 2008/106552 A1 | 9/2008 | |
| WO | 2008/112709 A1 | 9/2008 | |
| WO | 2008/133634 A1 | 11/2008 | |
| WO | 2009/154987 A1 | 12/2009 | |

OTHER PUBLICATIONS

Clearcount Medical Solutions, "The SmartSponge System," Downloaded from http://clearcount.com on Oct. 20, 2009, 7 pages.

Macario et al., "Initial Clinical Evaluation of a Handheld Device for Detecting Retained Surgical Gauze Sponges Using Radiofrequency Identification Technology," Arch Surg 141:659-662, Jul. 2006.

International Search Report, mailed Jan. 4, 2010, for PCT/US2009/045312, 3 pages.

Written Opinion, mailed Jan. 4, 2010, for PCT/US2009/045312, 3 pages.

Blair et al., "Tag and Detection Device," U.S. Appl. No. 60/458,222, filed Mar. 27, 2003, 23 pages.

Blair et al., "Improved Apparatus and Method for Detecting Objects Using Tags and Wideband Detection Device," U.S. Appl. No. 60/811,376, filed Jun. 6, 2006, 16 pages.

Blair et al., "Method, Apparatus and Article for Detection of Transponder Tagged Objects, for Example During Surgery," U.S. Appl. No. 60/892,208, filed Feb. 28, 2007, 50 pages.

Blair et al., "Transponder Housing and Device to Mark Implements, Such As Surgical Implements, and Method of Using Same," U.S. Appl. No. 60/894,435, filed Mar. 12, 2007, 30 pages.

Barnes et al., "Method, Apparatus and Article for Detection of Transponder Tagged Objects, For Example During Surgery," U.S. Appl. No. 61/056,787, filed May 28, 2008, 60 pages.

Blair, "Transponder Device to Mark Implements, Such As Surgical Implements, and Method of Manufacturing and Using Same," U.S. Appl. No. 61/086,727, filed Aug. 6, 2008, 30 pages.

Barnes et al., "Method, Apparatus and Article for Detection of Transponder Tagged Objects, for Example During Surgery," U.S. Appl. No. 61/091,667, filed Aug. 25, 2008, 76 pages.

Blair et al., "Method and Apparatus to Detect Transponder Tagged Objects, For Example During Surgery," U.S. Appl. No. 61/109,104, filed Oct. 28, 2008, 73 pages.

Blair, "Detectable Surgical Objects and Methods of Making Same," U.S. Appl. No. 61/109,142, filed Oct. 28, 2008, 47 pages.

Blair, "Transponder Device to Mark Implements, Such As Surgical Implements, and Method of Manufacturing and Using Same," U.S. Appl. No. 61/220,452, filed Jun. 25, 2009, 46 pages.

Blair et al., "Method and Apparatus to Detect Transponder Tagged Objects, For Example During Surgery," U.S. Appl. No. 61/222,443, filed Jul. 1, 2009, 95 pages.

Blair, "Radio Opaque Device with Resonant Nanostructures," U.S. Appl. No. 61/163,813, filed Mar. 26, 2009, 47 pages.

Blair et al., "Method and Apparatus to Detect Transponder Tagged Objects and to Communicate with Medical Telemetry Devices, For Example During Surgery," U.S. Appl. No. 61/222,847, filed Jul. 2, 2009, 122 pages.

Blair, "Transponder Device to Mark Implements, Such As Surgical Implements, and Method of Manufacturing and Using Same," U.S. Appl. No. 61/224,323, filed Jul. 9, 2009, 57 pages.

Blair et al., "Method and Apparatus to Detect Transponder Tagged Objects and to Communicate with Medical Telemetry Devices, For Example During Medical Procedures," U.S. Appl. No. 61/242,699, filed Sep. 15, 2009, 158 pages.

Blair, "Method and Apparatus to Account for Transponder Tagged Objects Used During Medical Procedures," U.S. Appl. No. 61/263,726, filed Nov. 23, 2009, 78 pages.

Blair et al., "Mat Based Antenna System to Detect Transponder Tagged Objects, For Example During Medical Procedures," U.S. Appl. No. 61/453,846, filed Mar. 17, 2011, 38 pages.

Blair, "Transponder Housing," U.S. Appl. No. 29/322,539, filed Aug. 6, 2008, 6 pages.

Blair, "Attachment Article to Attach a Transponder to a Surgical Sponge," U.S. Appl. No. 29/336,007, filed Apr. 27, 2009, 4 pages.

Blair, "Attachment Article to Attach a Transponder to a Surgical Sponge," U.S. Appl. No. 29/336,008, filed Apr. 27, 2009, 7 pages.

Blair, "Article to Attach a Transponder to a Surgical Sponge," U.S. Appl. No. 29/336,009, filed Apr. 27, 2009, 4 pages.

\* cited by examiner

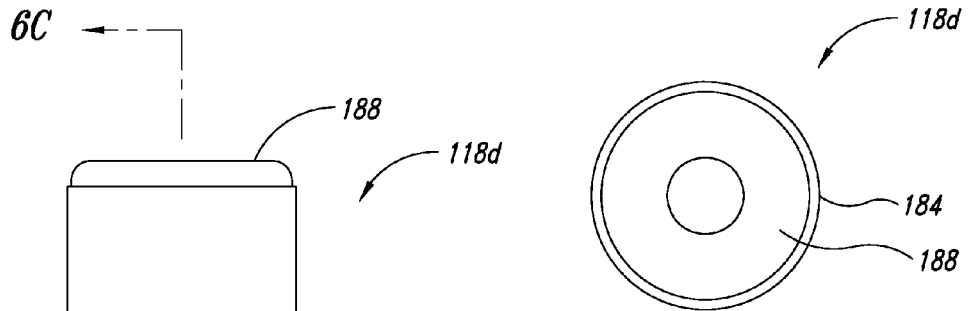
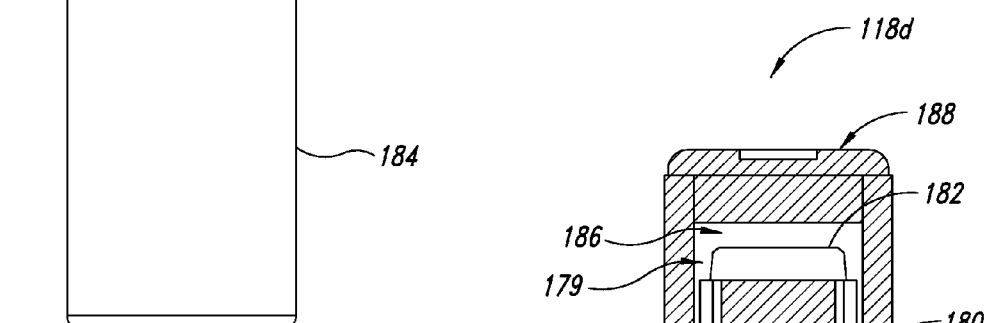
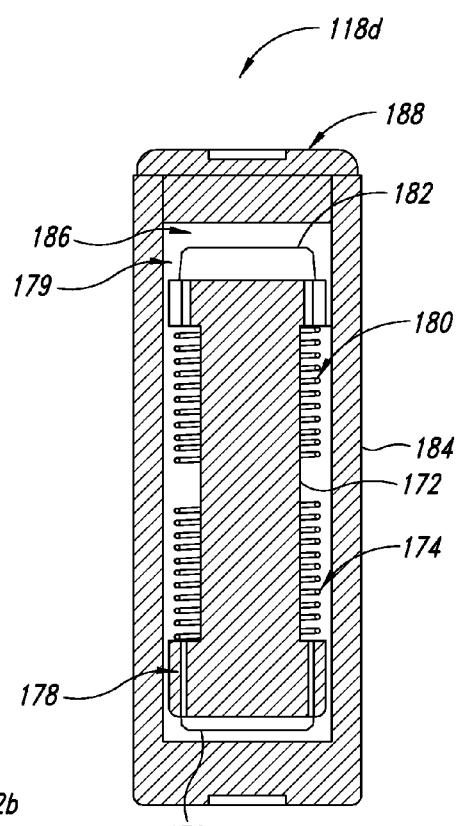
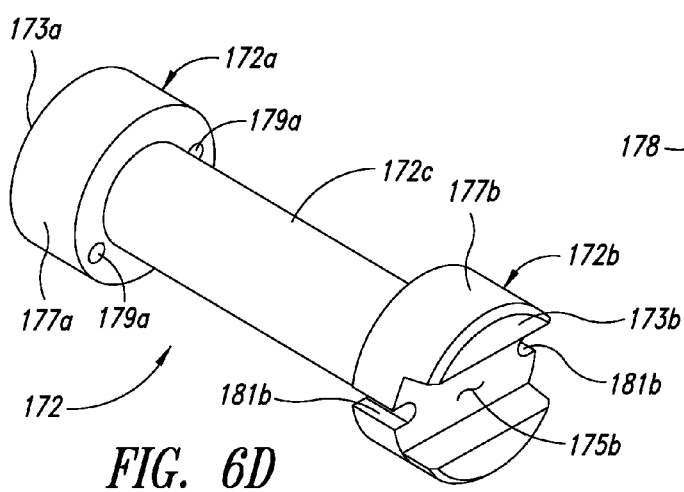
FIG. 6A
FIG. 6B
FIG. 6C
FIG. 6D

MULTI-MODAL TRANSPONDER AND METHOD AND APPARATUS TO DETECT SAME

CROSS-REFERENCE(S) TO RELATED APPLICATION(S)

This application claims the benefit under 35 U.S.C. §119 (e) of U.S. Provisional Patent Application Ser. No. 61/056,229, filed May 27, 2008 and U.S. Provisional Patent Application Ser. No. 61/102,749, filed Oct. 3, 2008.

BACKGROUND

1. Field

The present disclosure generally relates to detection of presence, or absence, and identification of objects tagged with transponders, which may, for example, allow detection and identification of surgical objects (e.g., sponges, instruments, etc.) during or after surgery, or for inventorying of objects, for instance surgical objects.

2. Description of the Related Art

It is often useful or important to be able to determine the presence or absence of an object.

For example, it is important to determine whether objects associated with surgery are present in a patient's body before completion of the surgery. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures which include checklists or require multiple counts to be performed to track the use and return of objects during surgery. Such manual approaches are inefficient, requiring the time of highly trained personnel, and are prone to error.

Another approach employs transponders and a wireless interrogation and detection system. Such an approach employs wireless transponders which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

However, some of these approaches do not allow identification of the object. Conventional approaches that allow identification of the object via transmitting an identifier typically transmit a signal at frequencies that have a short range of detection, which may inhibit detection of the transponder, and thus, the object attached thereto. Furthermore, these transponders may not be detectable by the interrogation device when they are situated such that there is an obstacle or membrane, such skin or flesh, between the transponder and the interrogation device.

Consequently, a new approach to uniquely identify and detect presence and absence of a transponder assembly as well as identification is desirable.

BRIEF SUMMARY

It may be useful for a medical provider to be able to detect a transponder at longer ranges while still being able to receive an identifier from the transponder to uniquely identify the object. For example, upon detecting that an object is present in a proximity of the surgical site, particularly inside the body of the patient, it may be useful to wirelessly determine an identity of the object. Further, upon completion of surgery, it may useful to scan the objects that were used during surgery and are currently present, to identify them and determine whether all of the objects that were present before surgery are present after surgery outside the patient's body without requiring a manual count of the objects by highly trained and highly compensated personnel. Additionally, identification of the object can also be useful in determining use history of an object, or the duration of time lapsed from a reference point in time relating to the object, such as a last maintenance time of the object. For example, in the medical or surgical context, tools such as those listed above, can have a limited shelf life after being disinfected and before being used or reused. Furthermore, some tools have a total life cycle after which they need to be replaced or go through maintenance before being reused. Conventional manual tracking of an object's life cycle, maintenance cycle, shelf life or any other parameter, even when assisted by computers, can be costly and time-consuming.

A system for detecting and identifying an object may be summarized as including an identification transponder including at least a first inductive winding and an integrated circuit that stores an identifier, the first inductive winding electrically coupled to the integrated circuit and operable to transmit an identification signal from the identification transponder in response to receipt of an interrogation signal in a first frequency range, the identification signal encoding an identifier stored by the integrated circuit, and a presence/absence transponder including a resonant inductive/capacitive tank circuit having at least a second inductive winding and a capacitor, the second inductive winding electrically coupled to the capacitor and operable to transmit a presence/absence signal from the presence/absence transponder in response to an interrogation signal in a second frequency range, the presence/absence response signal omitting any unique identifying information, the presence/absence transponder physically coupled to the identification transponder to form an integral detection and identification transponder that can selectively be attached to the object.

The system may further include an interrogation device configured to transmit a first interrogation signal in the first frequency range and at least a second interrogation signal in the second frequency range, the interrogation device including means for receiving the identification signal, and decoding the identifier, the interrogation device including means for receiving the presence/absence signal and providing an indication of presence of the object when the presence/absence signal is received.

The system may further include means for coupling the integral detection and identification transponder to the object without impeding performance of the object. The first inductive winding may include a first core portion and a first conductive wire wound about the first core portion and the second inductive winding may include a second core portion and a second conductive wire wound about the second core portion.

The system may further include a coupling member configured to attach the integral detection and identification transponder to the object without impeding performance of the object wherein at least one of the first core portion or the second core portion may include a hollow space, the coupling member extending from the hollow space. The coupling member may further physically couple the presence/absence transponder to the identification transponder. The first core portion may be coupled to the second core portion, and the first core portion and the second core portion may be made from a ferrite rod. The first core portion and the second core portion may be formed from a unitary body of material including a ferrite rod. The first core portion and the second core portion may form a common core and at least a portion of the first conductive wire may be interlaced with at least a portion of the second conductive wire around the common core.

The first core portion may include a first end portion having a first recess sized and dimensioned to receive a first electrical or electronic component (e.g., capacitor, integrated circuit, etc.). The first core portion may include a first perimeter having a first pair of slots that communicate with the first recess, which slots may be sized and dimensioned to receive a portion of a respective wire therein. The second core portion may include a second end portion having a pair of through-holes sized and dimensioned to receive a portion of a respective wire therethrough. Alternatively, the second core portion may include a second end portion having a second recess sized and dimensioned to receive a second electrical or electronic component (e.g., capacitor, integrated circuit, etc.). The second core portion may include a second perimeter having a second pair of slots that communicate with the second recess, the slots sized and dimensioned to receive a portion of a respective wire therein. A wall portion may be located between the first and the second end portions, the wall portion electrically insulating the first and the second inductive windings from each other.

The system may further include a bio-inert member encapsulating the integral detection and identification transponder. The identification transponder may be removably coupled to the presence/absence transponder. The integral detection and identification transponder may be flexible and at least a portion thereof may form a physical coupling member configured to directly physically couple to the object.

A system for detecting and identifying an object may be summarized as including an identification transponding means for transmitting an identification signal in response to a first interrogation signal, the identification signal including identification information that uniquely identifies the identification transponding means, and a presence/absence transponding means for transmitting a presence/absence signal in response to a second interrogation signal, the presence/absence signal excluding identification information that uniquely identifies the presence/absence transponder, the second interrogation signal different from the first interrogation signal, wherein the identification transponding means and the presence/absence transponding means are physically coupled to one another to form an integral detection and identification transponder configured to be selectively attached to the object.

The system may further include means for coupling the identification transponding means to the presence/absence transponding means.

The system may further include means for transmitting the first interrogation signal and the second interrogation signal, means for receiving the identification signal including means for reading the identification signal and providing an indication of the identification information, and means for receiving the presence/absence signal and providing an indication of presence or absence of the presence/absence transponding means. The identification transponding means may include an integrated circuit and a first antenna coupled to the integrated circuit and the presence/absence transponding means may include a capacitor and a second antenna coupled to the capacitor.

The system may further include a conductive core having a first portion and a second portion wherein the first antenna includes a conductive wire wound about the first portion of the conductive core, and the second antenna includes a conductive wire wound about the second portion of the conductive core. The conductive core may be made from a ferrite rod and may include a first end and a second end, the integrated circuit coupled to the conductive core toward the first end, and the capacitor coupled to the conductive core toward the second end.

The system may further include means for encapsulating the identification transponder and presence/absence transponder made from a bio-inert material. The first antenna may include a first core and a first inductive winding wound about the first core, and the second antenna may include a second core and a second inductive winding wound about the second core. The first core may include an outer wall, an inner wall, and an elongated portion extending between the outer wall and the inner wall, the first inductive winding wound about the intermediate portion of the first core, and the second core may include an outer wall, an inner wall, and an elongated portion extending between the outer wall and the inner wall, the second inductive winding wound about the intermediate portion of the second core, the inner wall of the first core coupled to the inner wall of the second core.

The system may further include a physical coupling member coupling the respective inner walls of the first core and the second core, the physical coupling member configured to couple the integral detection and identification transponder to the object. The second core may include a hollow space configured to insertably secure at least a portion of the identification transponding means.

A method of detecting and identifying a medical object coupled to a multi-mode integral detection and identification transponder having a resonant circuit transponder assembly and a radio frequency identification (RFID) transponder assembly may be summarized as including scanning a selected area by transmitting a first interrogation signal in a first frequency range at a first time, providing an indication of presence of the medical object when a presence/absence signal is transmitted from the resonant circuit transponder assembly in response to the first interrogation signal, transmitting a second interrogation signal having a second frequency in a second frequency range at a second time, receiving an identification signal, carrying identification information encoded in the RFID transponder assembly and associated with information corresponding to at least one attribute of the medical object, from the RFID transponder assembly in response to the second interrogation signal, and decoding the identification information and providing an indication of the identification information.

The method may further include storing the identification information onto an RFID tag of the RFID transponder assembly. The first time may be different from the second time. The selected area may include an area proximate to a surgical site. The second time may be subsequent to the first time when the presence/absence signal is received. The first time may include a time during or after surgery, and the second time may include a time at which an inventory is taken of the at least one attribute. The at least one attribute may include at least one of a life-cycle attribute, a maintenance schedule attribute, an identification attribute, or a use attribute. Transmitting the second interrogation signal may include scanning a selected area accommodating a plurality of medical objects each coupled to a distinct multi-mode integral detection and identification transponder, the receiving the information signal including receiving the information signal from the RFID transponder assembly of each transponder, the decoding the identification information and providing the indication of the identification information including decoding the identification information and providing the indication of the identification information corresponding to at least one attribute of each of the plurality of medical objects.

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 6A is a side elevational view of a detection and identification transponder, according to a further illustrated embodiment.

FIG. 6B is an end view of the detection and identification transponder of FIG. 6A.

FIG. 6C is a cross-sectional view of the detection and identification transponder of FIG. 6A, viewed across section 6C-6C.

FIG. 6D is an isometric view of a portion of the detection and identification transponder of FIG. 6A.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Further more, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
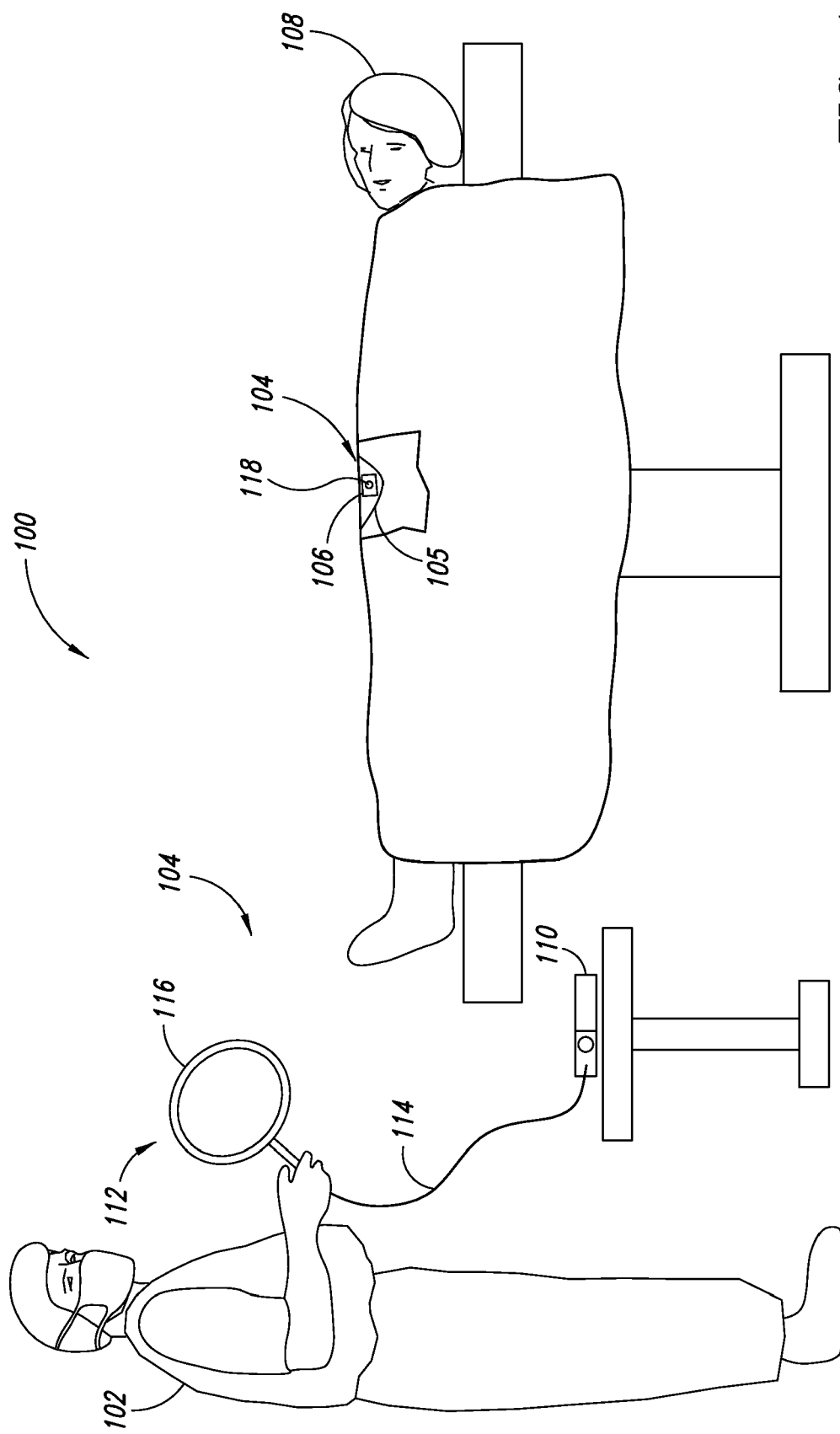
FIG. 1 is a schematic diagram illustrating a surgical environment where a medical provider uses an interrogation and detection system to detect an object tagged with a detection and identification transponder in a patient, according to one illustrated embodiment.

FIG. 1 shows a surgical environment 100 in which a medical provider 102 operates an identification and detection system 104 to ascertain the presence or absence of objects 106 in, or on, a patient 108, for example in or on a surgical site or area or cavity 105, and an identity of such objects 106. The identification and detection system 104 may include a controller 110, and an interrogation device or assembly, such as an antenna 112 coupled to the controller 110 by one or more communication paths, for example a coaxial cable 114. The antenna 112 may take the form of a hand-held wand 116.

The object 106 may take a variety of forms, for example instruments, accessories and/or disposable objects useful in performing surgical procedures. For instance, the object 106 may take the form of scalpels, scissors, forceps, hemostats, and/or clamps. Also for example, the objects 106 may take the form of surgical sponges, gauze and/or padding. The object 106 is tagged, carrying, attached or otherwise coupled to an integral detection and identification transponder 118.

As described in more detail with respect to some embodiments, in use, the medical provider 102 can position the wand 116 proximate the patient 108 within a first proximity in order to detect the presence or absence of the integral detection and identification transponder 118. In addition, the medical provider 102 can position the wand 116 proximate the patient 108 within a second proximity in order to identify the object 106 or an attribute of the object 106 by reading or receiving an identifier associated with the object 106.

Figure 2:
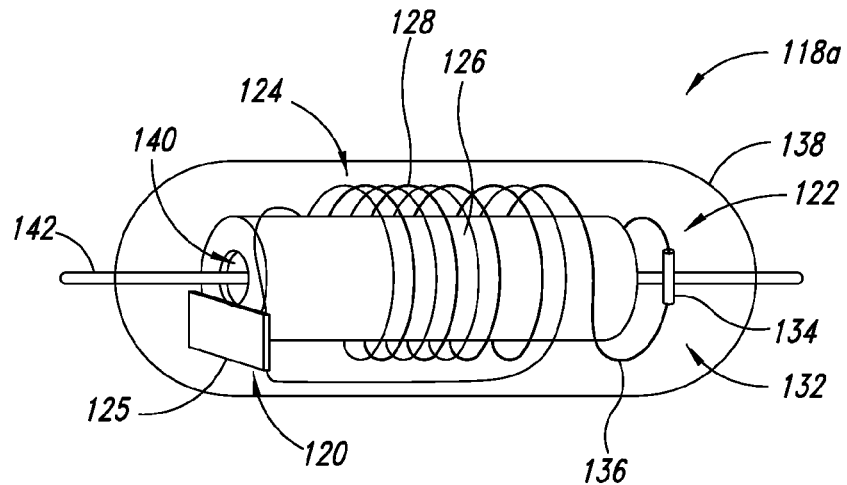
FIG. 2 is an isometric view of an integral detection and identification transponder, according to one illustrated embodiment.

FIG. 2 illustrates an integral detection and identification transponder 118a according to one embodiment. The integral detection and identification transponder 118a includes an identification transponder 120 and a presence/absence transponder 122, at least a portion of which is physically coupled to or shared with the identification transponder 120. The identification transponder 120 includes a first inductive winding 124, and a core 126 about which the first inductive winding 124 is wound. The first inductive winding 124 is electrically coupled to an integrated circuit 125, and is operable to transmit an identification signal from the identification transponder 120, in response to receiving an interrogation signal in a first frequency range. The identifier may be a unique identifier (i.e., unique over a set of all otherwise identical identification transponders 120). Alternatively, the identifier may not be unique, for example, a set of identification transponders 120 may each have the same identifier. Even where the identifier is unique, some portion of the identifier or some other identifier may not be unique, for example, a portion representing a manufacturer, a lot, or a type, may be shared between transponders from the same manufacturer, lot or of the same type. The identification signal encodes an identifier stored by the integrated circuit 125. The identifier can be associated with a type of the object 106 or an attribute thereof. For example, the identifier can be linked to the type or attribute using a database that cross-references unique identifiers with the type or attribute. In one aspect, the identification transponder 120 takes the form of a radio frequency identification device (RFID) transponder, including an RFID integrated circuit and/or front end.

The presence/absence transponder 122 includes a resonant inductive/capacitance (L/C) tank circuit. The resonant inductive/capacitance (L/C) tank circuit includes a second inductive winding 132 and a capacitor 134. The second inductive winding 132 may be interleaved with the first inductive winding 124 about a common core. For example, in the illustrated embodiment of FIG. 2, the second inductive winding 132 may be wound about an exterior surface of the same core 126 as the first inductive winding 124. As one example, the first and second inductive windings 124, 132 can take the form of a spiral wound conductive wire 128, 136 with one or more electrically insulative sheaths or sleeves. Further, the first and second inductive windings 124, 132 can be wound about distinct portions of the core 126, or as illustrated, they can be interleaved or otherwise interlaced about the core 126.

The second inductive winding 132 is electrically coupled to the capacitor 134, and is operable to transmit a presence/absence signal from the presence/absence transponder 122 in response to an interrogation in a second frequency range emitted from the wand 116. The presence/absence response signal does not include any unique identifying information. The presence/absence response signal transmitted by the presence/absence transponder 122 indicates that the presence/absence transponder 122 is present. Since the integral detection and identification transponder 118a is attached to the object 106, the presence/absence signal also conveys that the object 106 is present. When the medical provider 102 acknowledges the presence/absence signal and, thus, presence of the object 106, the medical provider 102 can then operate the antenna 112 or wand 116 at a frequency in the first range in order to identify the object 106. Based on this information, the medical provider 102 can make informed decisions with respect to the object 106, for example, decide on an optimum method or timing of removal of the object 106 from the surgical area or site, for example, sensing the object 106 before closing the patient.

Typically, the second range is greater than the first range even when the interrogation signal from the wand 116 supplies the same amount of energy to the detection and identification transponder 118a. This is because the resonant inductive/capacitance (L/C) tank circuit of the presence/absence transponder 122 is operable to transmit signals at lower frequencies and detectable at a greater range than the identification transponder 120. Furthermore, the wand 116 can detect the presence/absence signal transmitted by the presence/absence transponder 122 through a membrane or obstacle such as skin or flesh.

Upon detecting and removing the object or objects 106 from the body of the patient 108, and with all the present objects 106 laid out in an area after surgery and before closing the surgical site or area 105, the medical provider 102 can scan the present objects 106 to ensure that all the objects 106 that were present before surgery, are present and outside of the body of the patient 108 after surgery. Accordingly, the integral detection and identification transponder 118a provides the capability to efficiently detect objects 106 that may be present in or on the body of the patient 108, and the capability to conduct an inventory of present objects 106 after surgery to ensure all objects 106 used during surgery are present, without the use of multiple separately affixed tags or transponders and without the need to conduct a manual count of the objects by highly trained and highly paid personnel.

The respective identifiers stored on each of the integrated circuits 125 of the identification transponders 120 attached to the objects 106 can be linked to an attribute of the corresponding objects, such as the object's name or type, for example in a database, data structure or lookup table. Furthermore, the controller 110 of the interrogation device or assembly may include an interface that displays the name of the objects as the wand 116 scans the objects 106 after surgery. For example, the interface may display an accounting or inventory of sponges, gauzes, padding, hemostats, clamps, forceps, scissors, scalpels, or other surgical tools or accessories, or any other objects 106, for an expedient accounting of the objects 106. Alternatively, in embodiments where the respective integrated circuits 120 have read and write capability, the identifier can include the desired attribute, pre-stored or written onto the integrated circuit 120, and directly convey the pre-stored attribute via the identification signal.

The integral detection and identification transponder 118a may include an encapsulation 138 that encapsulates the core 126. In some embodiments, the core 126 can be fabricated from a ferrite rod. The ferrite rod may include a passage 140 sized to receive a physical coupler 142, for example a bonding tie or string. The bonding tie or string may take the form of an elastomeric X-ray opaque flexible elongated member that can be sized to attach the integral detection and identification transponder 118a to various types of objects 106, for example accessories such as surgical sponges and/or tools such as hemostats, forceps, scalpels, and scissors. In one aspect, the integral detection and identification transponder 118a can have a length of less than 15 millimeters, for example, 8 millimeters, and a diameter of less than 5 millimeters, for example, 2 millimeters. Employing small dimensions ensures that the transponder 118a does not impede the performance of the corresponding object 106, such as deformation of objects 106 such as sponges. Other dimensions are possible.

Figure 3:
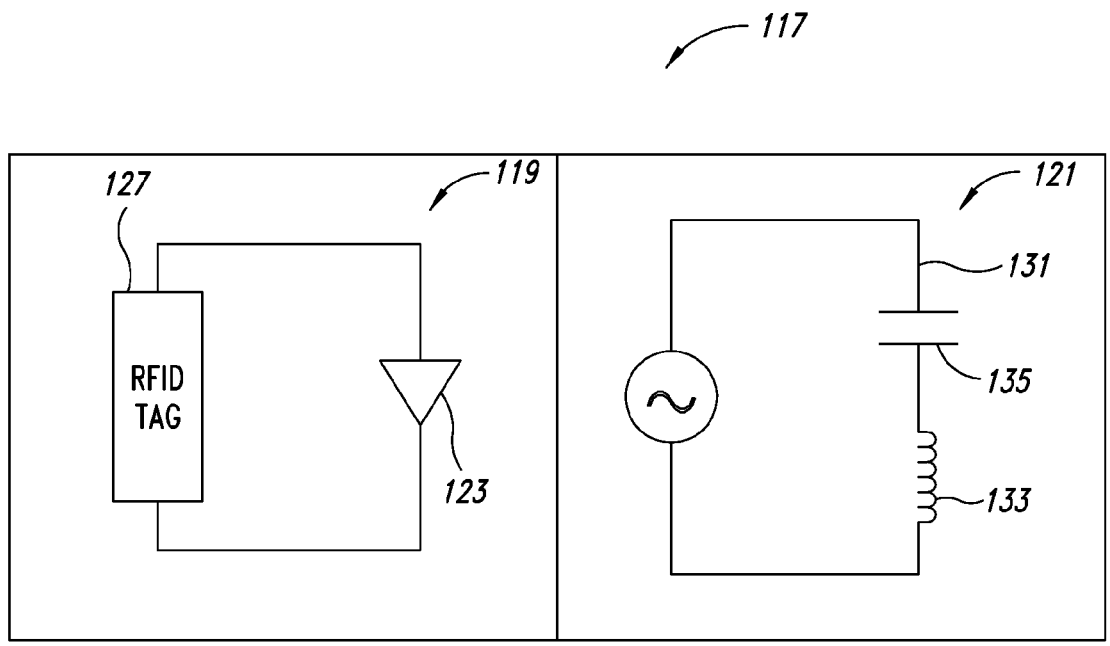
FIG. 3 is a schematic block diagram of an identification transponder circuit and resonant inductive/capacitance tank circuit according to another illustrated embodiment.

FIG. 3 illustrates a schematic block diagram of a generic embodiment of an integral detection and identification transponder 117. The detection and identification transponder 117 includes an identification transponder 119 and a presence/absence transponder 121. The presence/absence transponder 121 includes a resonant inductive/capacitance (L/C)

tank circuit 131 having an inductive winding 133 electrically coupled to a power storage device 135, for example, a capacitor. Furthermore, the identification transponder 119 includes an integrated circuit 127 electrically coupled to an antenna 123. In some embodiments, such as that in the illustrated embodiment of FIG. 2, the antenna can include an inductive winding such as a conductive wire wound about a core. The core can be fabricated from a ferrite rod.

Figure 4:
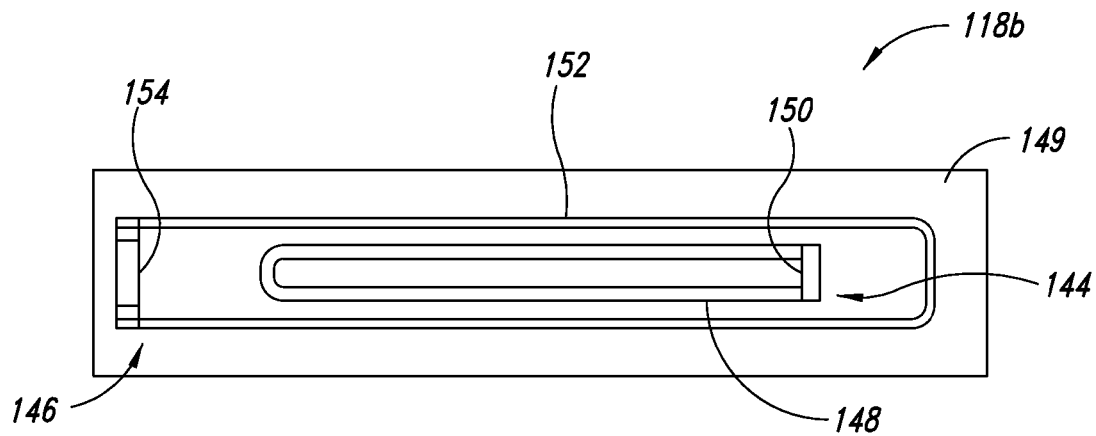
FIG. 4 is a side elevational view of an integral detection and identification transponder, according to yet another illustrated embodiment.

FIG. 4 shows an integral detection and identification transponder 118b according to another illustrated embodiment. The transponder 118b includes an identification transponder 144 and a presence/absence transponder 146.

The identification transponder 144 includes a first inductive winding 148 in the form of at least a first loop of conductive material, for example a loop of conductive wire. The first inductive winding 148 is electrically coupled in series to an integrated circuit 150. The presence/absence transponder 146 includes a second inductive winding 152 in the form of at least a second loop of conductive material, for example a loop of conductive wire. The second inductive winding 152 (L) is electrically coupled in series to a capacitor 154 (C) to form an LC series circuit. The second inductive winding 152 and capacitor 154 may be encapsulated in an elastomeric coating or sleeve 149. The dimensions of the transponder 118b may be similar to the dimensions of the transponder 118a of the embodiment discussed above. In some embodiments, the dimensions of the transponder 118b are greater than the dimensions of the transponder 118a of the embodiment discussed above. The detection and identification transponder 118b is highly flexible, and thus may provide its own thread-like or string-like attachment to various types of objects 106. Accordingly, a separate physical coupling member can be omitted, which can reduce the cost of manufacturing and purchasing large quantities of the transponder 118b, and also make it easier to affix and remove the transponder 118b from objects 106. A rigid coupling member may be preferred where the object 106 is metallic or contains metal in order to space the transponder 118b from the metallic portion or metal.

Similar to the previous embodiment, the identification transponder 144 transmits an identification signal via the first inductive winding 148 in response to receiving an interrogation signal in a first frequency range. The identification signal encodes an identifier stored by the integrated circuit 150. In one aspect, the identification transponder 144 takes the form of a radio frequency identification device (RFID) transponder, including an RFID integrated circuit and/or front end. Such may be a passive device, relying on energy in an interrogation signal to power the transponder. Accordingly, a user, such as the medical provider 102, by scanning the integral detection and identification transponder 118b can both detect presence or absence of objects 106, and upon detecting the presence of an object 106, the medical provider 102 can immediately scan the region of detection to identify the object 106 and make informed decisions with respect to handing of the object 106. For example, remove object prior to closing patent.

Figure 5:
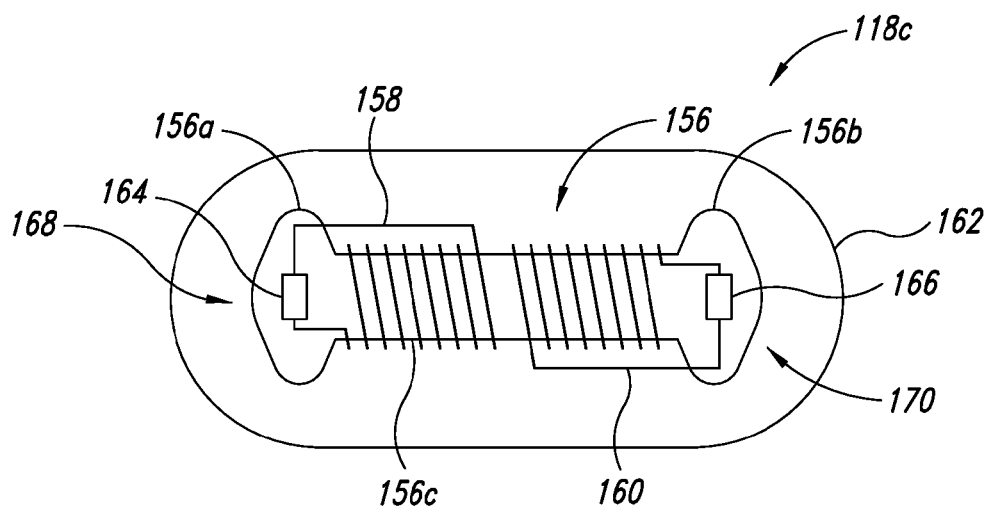
FIG. 5 is a side elevational view of an integral detection and identification transponder, according to still another illustrated embodiment.

FIG. 5 shows a detection and identification transponder 118c according to yet another embodiment. The transponder 118c includes a dumbbell-shaped ferrite rod 156 having broad end portions 156a, 156b, and a narrow intermediate portion 156c. The transponder 118c includes an identification transponder 168 and a presence/absence transponder 170. The identification transponder 168 includes a first inductive winding 158 electrically coupled to an integrated circuit 164. The presence/absence transponder includes a second inductive winding 160 electrically coupled to a capacitor 166. The broad portions 156a, 156b contain the first and the second inductive windings 158, 160. The transponder 118c may optionally include an encapsulant 162. In some embodiments, the transponder 118c may be formed as a fusiform-shaped object, with truncated ends.

Furthermore, in one aspect, the broad portions 156a, 156b can respectively mount the integrated circuit 164 and the capacitor 166. The fusiform shape may facilitate reducing the likelihood of close parallel alignment of multiple presence/absence transponders, which may produce transponder-to-transponder interaction and interference.

FIGS. 6A-6D illustrate a detection and identification transponder 118d according to a further embodiment. The detection and identification transponder 118d includes an identification transponder 178 and a presence/absence transponder 179. The identification transponder 178 includes a first inductive winding 174 wound about a ferrite core 172, and an integrated circuit 176 electrically coupled to the first inductive winding 174. The presence/absence transponder 179 includes a second inductive winding 180 and a capacitor (C) 182 electrically coupled to the second inductor 180 to form an LC series circuit. The transponder 118d also includes a capsule 184 with a cavity 186 open at least toward one end to receive the ferrite core 172, the first and the second inductive windings 174, 180, the integrated circuit 176, and the capacitor 182. The detection and identification transponder 118d may also include a lid 188 to close the open end of the capsule 184.

The ferrite core 172 may, for example, take the form of a soft ferrite drum, and may, for example, be formed of Nickel Zinc. Suitable ferrite cores 172 may be commercially available from TAK FERRITE as part no. L8A DR3X9 B=1.8 F=6 or from HUAH YOW under part no. 10R030090-77S. As illustrated in FIG. 6D, the drum may have a pair of larger diameter end portions 172a, 172b, with a smaller diameter intermediate portion 172c between the end portions 172a, 172b.

The end portions 172a, 172b may each have a face 173a, 173b, respectively, the faces 173a, 173b facing opposite one another. One or both of the faces 173a, 173b may include a recess 175b. The recess 175b may be sized and dimensioned to receive one or more electrical or electronic components (e.g., capacitor, integrated circuit). For example, the recess 175b may be sized such to receive an electrical or electronic component such that the electrical or electronic component does not extend above the surface of the face 173b. Such may allow a very compact design, which is advantageous for medical applications in which transponders must not physically interfere with the use of surgical objects, such as sponges and/or instruments. Such may also provide a more secure physical coupling of the electrical or electronic components, preventing damage and thus failure of a transponder.

The end portions 172a, 172b may each have a perimeter 177a, 177b that forms an edge. One or both of the end portions 172a, 172b may include one or more through-holes 179a. One or both of the perimeters 177a, 177b may include one or more slots 181b that extends into the recess 175b. The through-holes 179a and the slots 181b are sized and dimensioned to receive electrical conductors, for example wires. Preferably, the slots 181b are sized and dimensioned to completely receive the electrical conductors, such that the electrical conductors do not extend above a surface of the perimeter 177b. Such may allow a very compact design, which is advantageous for medical applications in which transponders must not physically interfere with the use of surgical objects, such as sponges and/or instruments. Such may also provide a more secure physical coupling of the electrical conductors (e.g., wires), preventing damage and thus failure of a transponder.

The electrical conductors may thus extend from the electrical or electronic components secured on face 173a or in the recess 175b formed in face 173b, through the through-holes 179a or slots 181b, to the intermediate portion 172c, about which portions of the electrical conductors may be wound to form inductors. The end portions 172a, 172b may advantageously serve as a stops for the electrical conductors that form the windings of the inductors.

The first and the second inductive windings 174, 180 may take the form of magnet wire wound around the intermediate portion 172c of the ferrite core 172. The magnet wire may, for example, have a dimension of approximately 41 American Wire Gauge (AWG), although some embodiments may employ wires or conductors of larger or small gauges. Suitable inductive windings may be commercially available from ELEKTISOLA under part no. PN-155 or from ROSEN under part no. 2UEW-F. The second inductive winding 180 of the presence/absence transponder 179 may, for example, include approximately 432 turns, over approximately 6.5 layers, although some embodiments may include a greater or lesser number of turns and/or layers. The detection and identification transponder 118d may include tape and/or epoxy enveloping the first and the second inductive windings 174, 180. Suitable tape may be commercially available from 3M under part nos. 1298, 1350-1 or PLEO 1P801, while suitable epoxy may be commercially available from LOCKTITE under part no. 3211.

The capacitor 182 may, for example, take the form of a ceramic capacitor. The capacitor 182 may, for example, have a capacitance of 470 PF, 100V, with a Quality factor of Q>2200@1 MHz. Suitable capacitors may be commercially available from SANJV DIELECTRIC under part no. 0805NPO471J101 or from FENG HUA under part no. 0805CG471J101 NT.

The capsule 184 and lid 188 may, for example, be formed of a polypropylene. Suitable capsules 184 and lids 188 may be commercially available from WEITHE ELECTRON (HK) COMPANY, under part specification CASE 4.3×12.6. The combination of the capsule 184 and lid 188 may, for example, have a length of less than 20 millimeters, for example, approximately 12.8 millimeters, and a diameter of less than 10 millimeters, for example 4.4 millimeters. Other embodiments may have larger or smaller dimensions. Circuit bonds may, for example, employ UNITED RESINS CORP. part no. 63001500 CIRCUIT BOND LV, while solder may take the form of a lead free 96.5% Ag/3% Sn/0.5 Cu solder.

Such an embodiment may be useful in that the capsule 184 and lid 188 may provide improved protection of the electrical components of the detection and identification transponder 118d. Further, it may be easier to remove and repair or replace electrical components, allowing the capsule 184 and lid 188 to be reused (in contrast to conventional encapsulants) and further reducing costs associated with the detection and identification transponder 118d, especially when purchased or refurbished in large quantities.

Of the foregoing embodiments, those which include a core discuss detection and identification transponders 118a, 118c, 118d, which respectively include cores 126, 156, 172 that are each shared as a common core between the respective inductive windings 124, 158, 174 of the identification transponders 120, 168, 178 and the corresponding inductive windings 132, 160, 180 of the presence/absence transponders 122, 170, 179. However, one of ordinary skill in the art will appreciate that maintaining the integral nature of the detection and identification transponder can be preserved while the respective inductors are associated with distinct cores instead of a shared core.

Figure 7:
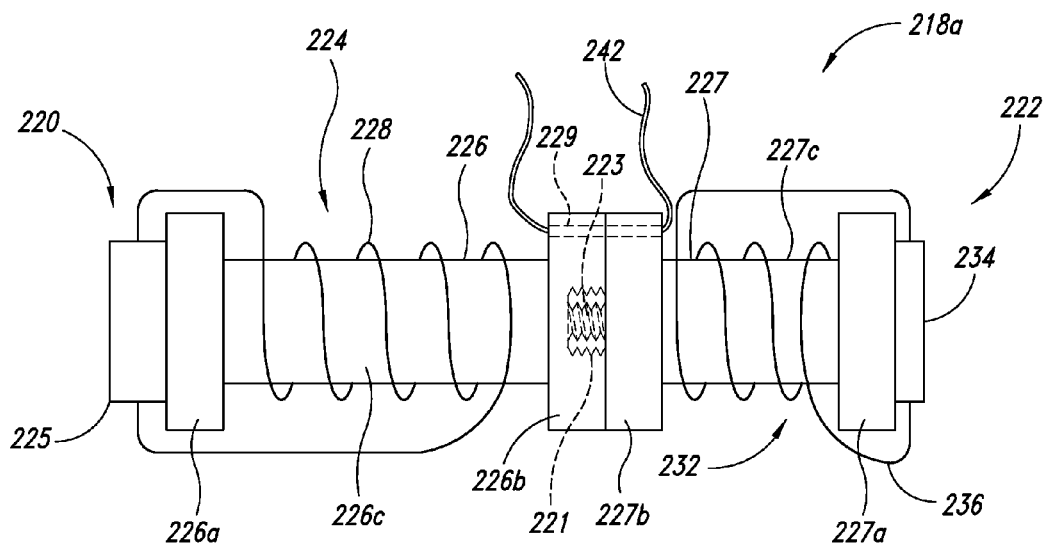
FIG. 7 is a side elevational view of an integral detection and identification transponder including a first part that is coupleable to a second part, according to yet a further illustrated embodiment.

For example, FIG. 7 illustrates a detection and identification transponder 218a according to yet a further embodiment. The detection and identification transponder 218a includes an identification transponder assembly 220 and a presence/absence transponder assembly 222, which is physically coupled to the identification transponder assembly 220. The identification transponder assembly 220 includes a first core 226 and a first inductive winding 224 wound about an exterior surface of the first core 226. The first inductive winding 224 is electrically coupled to an integrated circuit 225, and is operable to transmit an identification signal from the identification transponder 220, in response to receiving an interrogation signal in a first frequency range emitted from an interrogation assembly, similar to the wand 116 illustrated in FIG. 1. The identification signal encodes an identifier stored by the integrated circuit 226. In one aspect, the identification transponder 220 takes the form of a radio frequency identification device (RFID) transponder, including an RFID integrated circuit and/or front end.

The presence/absence transponder 222 includes a second core 227, a second inductive winding 232 wound about an exterior surface of the second core 227, and a capacitor 234 electrically coupled to the second inductive winding 232. The presence/absence transponder 222 is operable to transmit a presence/absence signal in response to an interrogation signal in a second frequency range emitted from the interrogation assembly. As one example, the first and second inductive windings 224, 232 can take the form of spiral wound conductive wires 228, 236 with an electrically insulative sheath or sleeve.

The identification transponder assembly 220 can be physically coupled to the presence/absence transponder assembly 222 in any suitable manner. For example, in the illustrated embodiment of FIG. 7, the first core 226 is physically coupled to the second core 227, integrating the identification transponder assembly 220 and the presence/absence transponder assembly 222 into a single device that can be attached to an object such as the object 106 illustrated in FIG. 1. In one embodiment, the first core 226 includes an outer wall 226a, an inner wall 226b, and an elongated intermediate portion 226c extending between the outer and inner walls 226a, 226b. The intermediate portion 226c has a smaller diameter than the outer and inner walls 226a, 226b. The first inductive winding 224 may be wound about the intermediate portion 226c. Similarly, the second core 227 includes an outer wall 227a, an inner wall 227b, and an elongated intermediate portion 227c extending between the outer and inner walls 227a, 227b, the intermediate portion 227c having a diameter smaller than the respective diameters of the outer and inner walls 227a, 227b. The second inductive winding 232 may be wound about the intermediate portion 227c.

Therefore, each of the first and the second cores 226, 227 include a spool-like shape that facilitates retention of the respective inductive windings 224, 232. Furthermore, the inner wall 226b of the first core 226 may be physically coupled to the inner wall 227b of the second core 227. Accordingly, in such an embodiment, the inner walls 226b, 227b facilitate integration of the identification and detection transponder 218a. Additionally, the outer wall 226a of the first core 226 can mount the integrated circuit 225, for example an RFID tag, while the outer wall 227a of the second core 227 can mount the capacitor 234. Similar to embodiments above, the detection and identification transponder 218a can also be encapsulated in a bio-inert material, which is not shown in FIG. 7 for clarity of illustration and description.

Therefore, a user, such as the medical provider 102 can scan an area, such as a surgical site or area, with the wand 116 in the second frequency range for detection of the presence/absence signal. Upon detecting the presence/absence signal, and thus presence of the object 106, the medical provider 102 can then operate the interrogation assembly in the first frequency range, which is typically a range shorter than the first frequency range, in order to identify the object 106 and based on this information, make informed decision with respect to the object, for example, decide on an optimum method or timing of removal of the object 106 from the surgical site or area, for example, sensing the object 106 before closing the patient.

Upon detecting and removing the object or objects 106 from the body of the patient 108, and with all the present objects 106 laid out in an area after surgery and before closing the surgical site or area 105, the medical provider can scan the objects 106 to ensure that all the objects 106 that were present before surgery, are present and outside of the body of the patient 108 after surgery. Accordingly, the integral detection and identification transponder 118a provides the capability to efficiently detect objects 106 that may be present in or on the body of the patient 108, and conduct an inventory of present objects after surgery to ensure all objects 106 used during surgery are present, without the use of multiple separately affixed tags or transponder, and without the need to conduct a manual count of the objects.

In one aspect, the identification transponder assembly 220 is removably coupled to the presence/absence transponder assembly 222. Such a configuration would allow the user to remove and replace one of the identification or the presence/absence transponder assemblies 220, 222, for example due to damage or defects present in one of these assemblies. For example, the presence/absence transponder assembly 222 can include a threaded protrusion 223 that threadedly couples to a threaded cavity 221 formed in the identification transponder assembly 220. Other suitable coupling methods are possible and contemplated to be within the scope of the present disclosure including the claims that follow. For example, the identification and presence/absence transponder assemblies 220, 222 can be coupled via an appropriate adhesive, a detent mechanism, magnets, or any other suitable coupling method. Where magnets are used, a shield cover (not shown) may be utilized over the inner walls 226b, 227b shielding effects of the magnets on transmission of the response signals from the identification and presence/absence transponder assemblies 220, 222.

Furthermore, in some embodiments, the first and the second cores 226, 227 can be hollow to allow a string or other attachment device or element to pass therethrough and attach the detection and identification transponder 218a to the object 106. Alternatively, as illustrated in FIG. 7, any of the inner and/or outer walls 226a, 226b, 227a, 227b may include a structural feature 229 that facilitates attaching the detection and identification transponder 218a to the object 106. For example, the structural feature 229 can include an aperture extending through a width of the inner walls 226b, 227b of the first and the second cores 226, 227, respectively, allowing a physical coupler 242, for example a bonding tie or string, to pass therethrough. The bonding tie or string may take the form of an elastomeric X-ray opaque flexible elongated member that can be used to attach the integral detection and identification transponder 218a to various types of objects 106, for example surgical sponges, hemostats, clamps, forceps, scissors, or any other surgical tools or accessories, or any other object. In some embodiments, the physical coupler 242 can couple the first core 226 to the second core 227, and also be configured to couple the detection and identification transponder 222 to the object 106.

Figure 8:
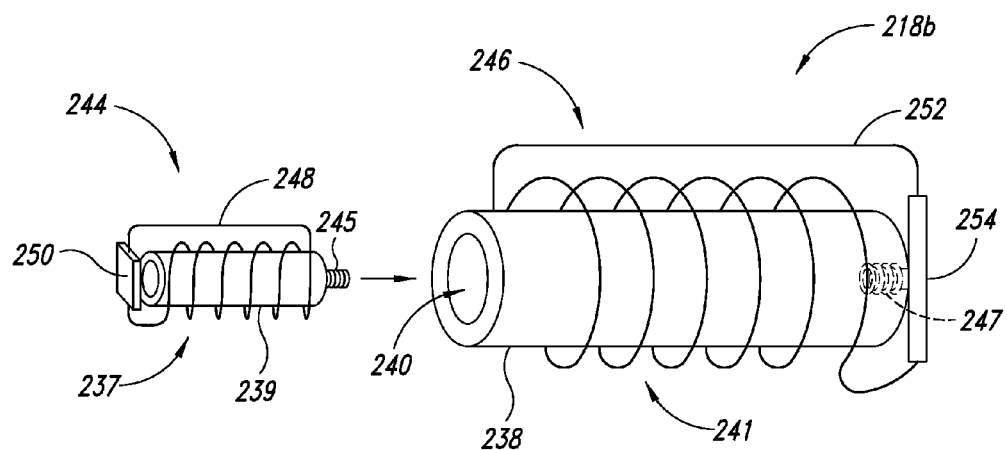
FIG. 8 is an isometric view of an integral detection and identification transponder including a first part that is received by a second part, according to still a further illustrated embodiment.

FIG. 8 illustrates yet a further embodiment of a detection and identification transponder 218b. The detection and identification transponder 218b includes an identification transponder assembly 244 and a presence/absence transponder assembly 246, which is physically coupled to the identification transponder assembly 244. The identification transponder assembly 244 includes a first core 239 and a first inductive winding 237 wound about an outer surface of the first core 239. The identification transponder assembly 244 further includes an integrated circuit 250. The first inductive winding 237 is electrically coupled to the integrated circuit 250, and is operable to transmit an identification signal from the identification transponder assembly 244, in response to receiving an interrogation signal in a first frequency range. Similar to other embodiments, the identification signal encodes an identifier stored by the integrated circuit 250. In one aspect, the identification transponder 244 takes the form of a radio frequency identification device (RFID) transponder, including an RFID integrated circuit and/or front end.

The presence/absence transponder assembly 246 includes a second core 238 and a second inductive winding 241 wound about an outer surface of the second core 238. The presence/absence transponder assembly 246 further includes a capacitor 234. The second inductive winding 241 is electrically coupled to the capacitor 234, and is operable to transmit a presence/absence signal from the presence/absence transponder assembly 246 in response to an interrogation in a second frequency range emitted from an interrogation assembly.

In the illustrated embodiment of FIG. 8, the identification transponder assembly 244 is concentrically physically coupled to the presence/absence transponder assembly 246. For example, the identification transponder assembly 244 can be sized to insertably receive and secure within a hollow 240 formed in the second core 238 of the presence/absence transponder assembly 246. The identification transponder assembly 244 can be secured within the hollow 240 in any suitable manner. For example, an outer surface of the identification transponder assembly 244, such as an outer surface of the first core 239 or an encapsulation (not shown) about the transponder assembly 244, may include a structural feature 245 configured to be coupled to a complementary structural feature 247 associated with the presence/absence transponder assembly 246 within the hollow 240.

For example, the first structural feature 245 can include a threaded protrusion, and the complementary structural feature 247 can include a cavity configured to threadedly couple to the threaded protrusion. Alternatively, the structural features 245, 247 may include complementary detent mechanism that can snap into and away from one another. Adhesives can also be used to physically couple the identification transponder assembly 244 to the presence/absence transponder assembly 246.

Additionally, or alternatively, each of the identification and the presence/absence transponder assemblies 244, 246 can include respective encapsulations, the encapsulation of the presence/absence transponder assembly 246 extending to cover inner surfaces of the hollow 240 and leaving open an end of the hollow 240 for receiving the identification transponder assembly 244. The encapsulations can be made from a bio-inert material that also exhibits at least some frictional qualities, such that when the identification transponder assembly 244 is inserted in the hollow 240, it is retained therein by frictional contact between the surfaces of the respective encapsulations.

Figure 9:
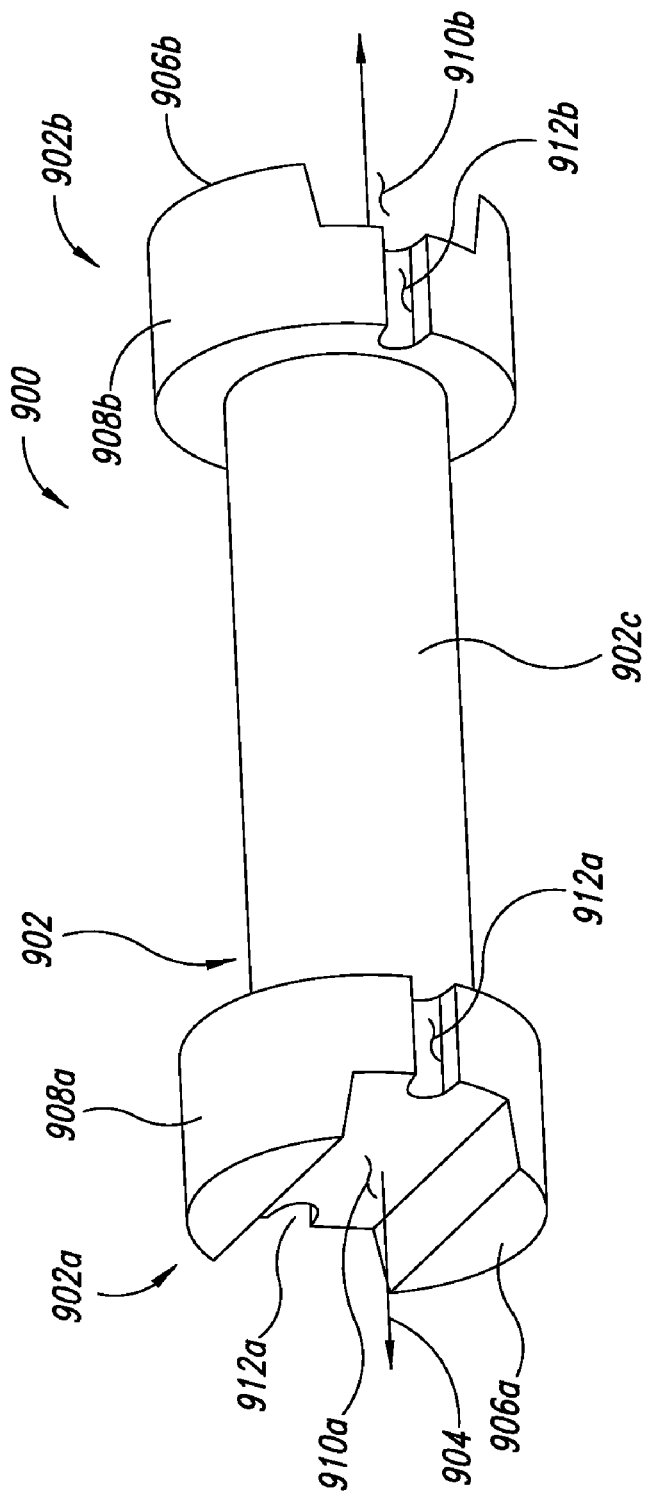
FIG. 9 is an isometric view of a transponder core, according to one illustrated embodiment.

FIG. 9 shows a ferrite core 900 suitable for use in a detection and identification transponder, according to a further embodiment.

As with previously described embodiments, the ferrite core 900 may, for example, take the form of a soft ferrite drum or dumbbell, and may, for instance, be formed of Nickel Zinc. The ferrite core 900 includes an elongated body 902 having a pair of relatively larger diameter end portions 902a, 902b and at least one relatively smaller diameter intermediate portion 902c located between the end portions 902a, 902b.

The elongated body 900 may extend along a longitudinal axis 904, although is not necessarily a body of revolution. The end portions 902a, 902b each have a face 906a, 906b, respectively, that is at least approximately perpendicular to the longitudinal axis 904, the faces 906a, 906b each facing in oppose directions to one another. The end portions 902a, 902b each have a perimeter 908a, 908b, respectively. The perimeters 908a, 908b may extend about the longitudinal axis 904. The body 902 may, for example, be cylindrical, although embodiments with non-circular cross sections (e.g., rectangular, square, hexagon, octagon, etc.) are possible.

Each of the faces 906a, 906b has a recess 910a, 910b, respectively, formed therein. The recesses 910a, 910b may be sized and dimensioned to receive at least a portion of an electrical or electronic component. Preferably, the recesses 910a, 910b may be sized and dimensioned to completely receive a respective electrical or electronic component such that the electrical or electronic component does not extend above a plane of the face 906a, 906b. Such may allow a very compact design, which is advantageous for medical applications in which transponders must not physically interfere with the use of surgical objects, such as sponges and/or instruments. Such may also provide a more secure physical coupling of the electrical or electronic components, preventing damage and thus failure of a transponder. For example, one recess 910a may be sized and dimensioned to receive an integrated circuit (not shown in FIG. 9). Also, for example, one recess 910b may be sized and dimensioned to receive a capacitor (not shown in FIG. 9).

The perimeters 908a, 908b each have a respective pair of opposed slots 912a, 912b, that extend to the recess 910a, 910b of the respective face 906a, 906b. The slots 912a, 912b may be sized and dimensioned to at least partially receive electrical conductors (not shown in FIG. 9), for example conductive wires such as magnet wires. Preferably, the slots 912a, 912b are sized and dimensioned to completely receive the electrical conductors, such that the electrical conductors do not extend above a surface of the perimeter 908a, 908b. Such may allow a very compact design, which is advantageous for medical applications in which transponders must not physically interfere with the use of surgical objects, such as sponges and/or instruments. Such may also provide a more secure physical coupling of the electrical conductors (e.g., wires), preventing damage and thus failure of a transponder.

The electrical conductors may thus extend from the electrical or electronic components secured in the recess 910a, 910b, through the slots 912a, 912b, to the intermediate portion 902c, about which portions of the electrical conductors may be wound to form inductors. The faces 906a, 906b may advantageously serve as stops for the electrical conductors that form the windings of the inductors. As in accord with previously described embodiments, tape and/or epoxy may cover the inductors.

Figure 10:
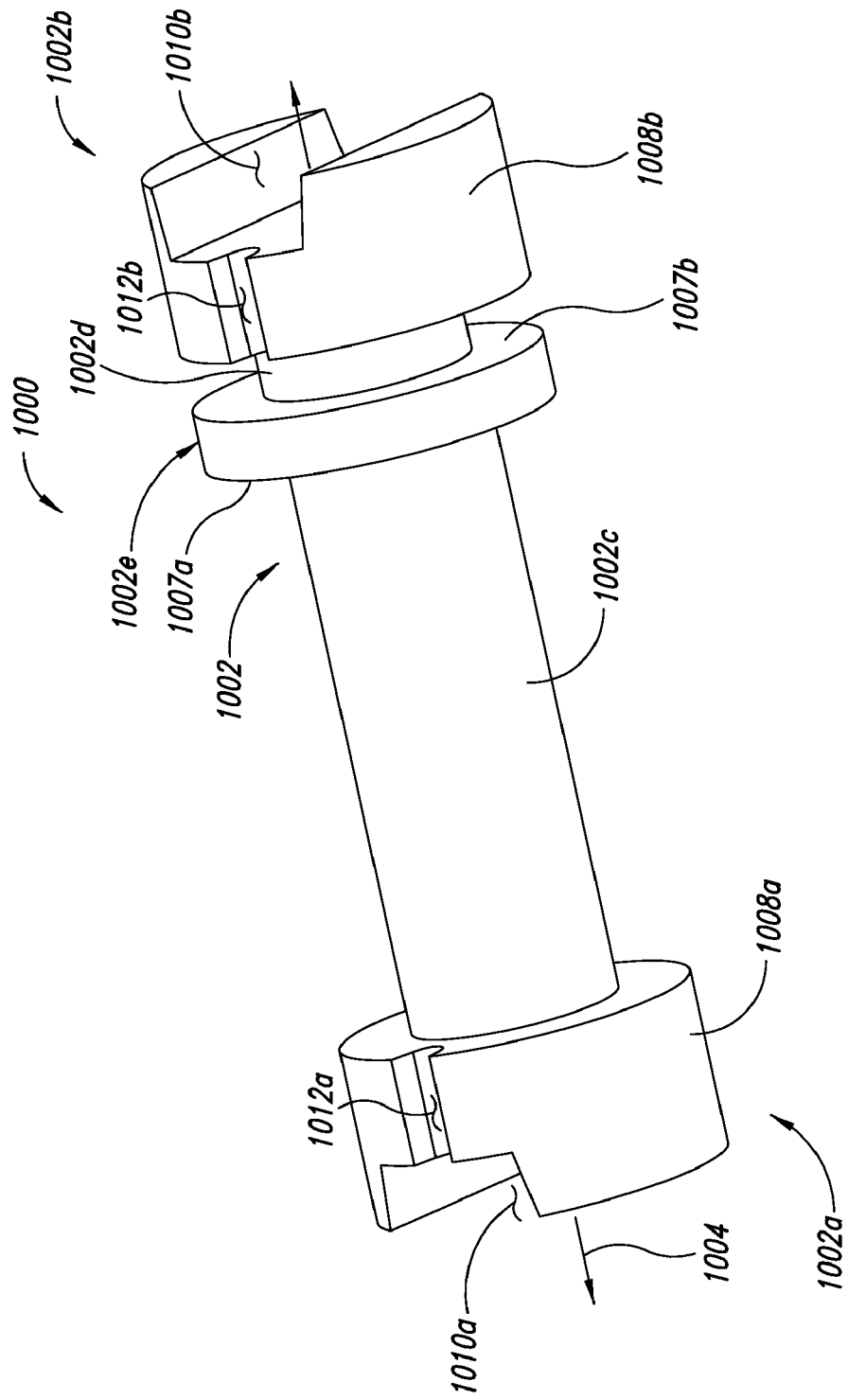
FIG. 10 is an isometric view of a transponder core, according to another illustrated embodiment.
Figure 11:
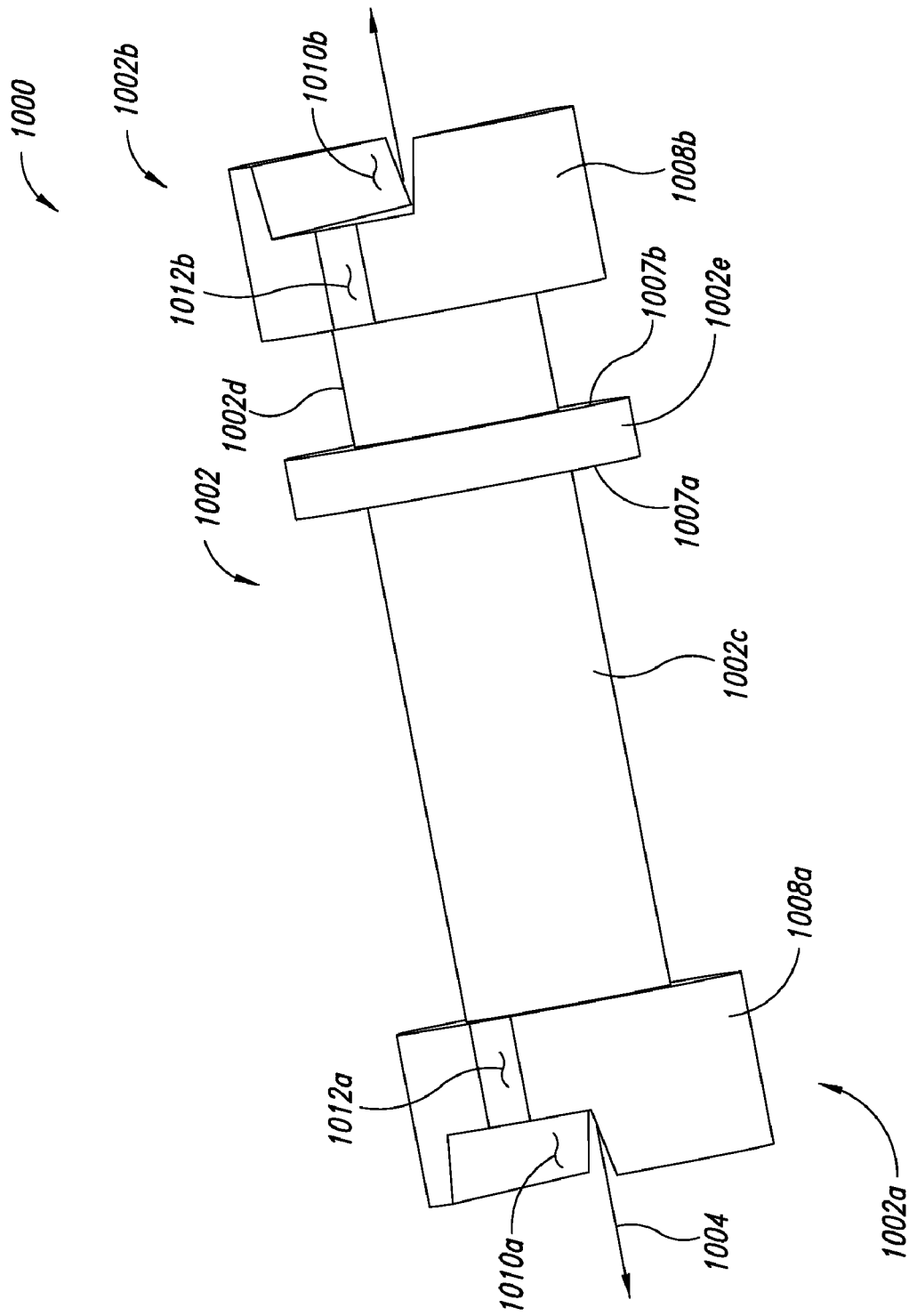
FIG. 11 is another isometric view of a transponder core of FIG. 10.

FIGS. 10 and 11 shows a ferrite core 1000 suitable for use in a detection and identification transponder, according to an even further embodiment.

As with previously described embodiments, the ferrite core 1000 may, for example, take the form of a soft ferrite drum or dumbbell, and may, for example, be formed of Nickel Zinc (Ni Zn) or possibly Manganese Zinc (MnZn). The ferrite core 1000 includes an elongated body 1002 having a pair of relatively larger diameter end portions 1002a, 1002b, a relatively large wall portion 1002e, and two relatively smaller diameter intermediate portions 1002c, 1002d located between the wall portion 1002e and respective ones of the end portions 1002a, 1002b. As illustrated, the intermediate portions 1002c, 1002d may be of different lengths from one another, although some embodiments may employ intermediate portions 1002c, 1002d or equal lengths.

The elongated body 1000 may extend along a longitudinal axis 1004. The end portions 1002a, 1002b each have a face 1006a, 1006b, respectively, that is at least approximately perpendicular to the longitudinal axis 1004, the faces 1006a, 1006b each facing in oppose directions to one another. Likewise, the wall portion 1002e has a pair of opposed faces 1007a, 1007b, that are at least approximately perpendicular to the longitudinal axis 1004, the faces 1007a, 1007b each facing in oppose directions to one another. The end portions 1002a, 1002b each have a perimeter 1008a, 1008b, respectively. The perimeters 1008a, 1008b may extend about the longitudinal axis 1004, although are not necessarily bodies of revolution. The wall portion 1002e has a perimeter 1008c. The perimeter 1008c of the wall portion 1002e may extend about the longitudinal axis 1004, although is not necessarily a body of revolution. The perimeter 1008c of the wall portion 1002e may be the same shape and/or size as the perimeters 1008a, 1008b of the end portions 1002a, 1002b, respectively. Alternatively, the perimeter 1008c of the wall portion 1002e may be a different shape and/or size than the perimeters 1008a, 1008b of the end portions 1002a, 1002b, for example having a smaller cross-sectional area (e.g., smaller circumference, radius or diameter). Additionally, the perimeter 1008c of the wall portion 1002e may have a different thickness than the perimeters 1008a, 1008b of the end portions 1002a, 1002b, for example having a smaller thickness. The body 1002 or portions there, may, for example, be cylindrical, although embodiments with non-circular cross sections (e.g., rectangular, square, hexagon, octagon, etc.) are possible.

Each of the faces 1006a, 1006b of the end portions 1002a, 1002b has a recess 1010a, 1010b, respectively, formed therein. The recesses 1010a, 1010b may be sized and dimensioned to receive at least a portion of an electrical or electronic component. Preferably, the recesses 1010a, 1010b may be sized and dimensioned to completely receive a respective electrical or electronic component such that the electrical or electronic component does not extend above a plane of the respective faces 1006a, 1006b. Such may allow a very compact design, which is advantageous for medical applications in which transponders must not physically interfere with the use of surgical objects, such as sponges and/or instruments. Such may also provide a more secure physical coupling of the electrical or electronic components, preventing damage and thus failure of a transponder. For example, one recess 1010a may be sized and dimensioned to receive an integrated circuit (not shown in FIG. 10 or 11). Also, for example, one recess 1010b may be sized and dimensioned to receive a capacitor (not shown in FIG. 10 or 11).

The perimeters 1008a, 1008b of the end portions 1002a, 1002b each have a respective pair of opposed slots 1012a, 1012b, that extend to the recess 1010a, 1010b of the respective face 1006a, 1006b. The slots 1012a, 1012b may be sized and dimensioned to at least partially receive electrical conductors (not shown in FIG. 10 or 11), for example conductive wires such as magnet wires. Preferably, the slots 1012a, 1012b are sized and dimensioned to completely receive the electrical conductors, such that the electrical conductors do not extend above a surface of the respective perimeters 1008a, 1008b. Such may allow a very compact design, which is advantageous for medical applications in which transponders must not physically interfere with the use of surgical objects, such as sponges and/or instruments. Such may also provide a more secure physical coupling of the electrical conductors (e.g., wires), preventing damage and thus failure of a transponder.

The electrical conductors may thus extend from the electrical or electronic components secured in the recess 1010a, 1010b, through the slots 1012a, 1012b, to the intermediate portion 1002c, about which portions of the electrical conductors may be wound to form inductors. The faces 1006a, 1006b of the end portions 1002a, 1002b and the faces 1007a, 1007b of the wall portion 1002e advantageously serve as stops for the electrical conductors that form the windings of the inductors. The wall portion 1002e also advantageously serves to electrically insulate the electrical conductors forming the inductors from one another. As in accord with previously described embodiments, tape and/or epoxy may envelope inductors.

In one embodiment, the ferrite core 1000 may have an overall length of approximately 11.0 mm, the large diameter end portions 1002a, 1002b may each have a length or thickness of approximately 1.5 mm, the large wall portion 1002e may have a length or thickness of approximately 1.0 mm, while the lengths of the intermediate portions 1002c, 1002d respectively between the large wall portion 1002e and a first one of the large diameter end portions 1002a may be approximately 6.0 mm and between the large wall portion 1002e and a second one of the large diameter end portions 1002b may be approximately 1.0 mm. The large diameter end portions 1002a, 1002b and large wall portion 1002e may each have diameters of approximately 3.0 mm, while smaller diameter intermediate portions 1002c, 1002d may each have diameters of approximately 1.8 mm. The recesses 1010a, 1010b may have a width of approximately 1.6 mm at an outer portion surface and approximately 1.4 mm at an inner portion, thus may taper inwardly from the outermost portion toward a bottom of the recess. The slots 1012a, 1012b may have a width of approximately 0.4 mm and a depth of approximately 0.4 mm.

In another embodiment, the ferrite core 1000 may have an overall length of approximately 9.5 mm, with a length between the large wall portion 1002e and a first one of the large diameter end portions 1002a of approximately 4.5 mm, the other dimension remaining the same or similar to the dimensions of the previously described embodiment.

In the disclosed embodiments, the detection and identification transponders 118a-118d, 218a, 218b, can each be part of a corresponding detection and identification system that includes an interrogation device similar to the antenna 112 having a wand 116 (FIG. 1). The wand 116 can be configured to emit the first interrogation signal in the first frequency range and include an integrated circuit tag reader, such as an RFID reader as is known, to receive the identification signal, and decode the identifier. The wand 116 can further be configured to emit the second interrogation signal in the second frequency and to receive the presence/absence signal to provide an indication of presence of the object when the presence/absence signal is received. Specific details of components of the wand 116 are not discussed herein to not unnecessarily obscure the description of the embodiments. Components configured for emission of the interrogation signals and for receiving the presence/absence signal can be selected from any suitable scanning technology, including, but not limited to, the detection device disclosed in U.S. Pat. No. 6,026,818, to Blair et al, and that disclosed in U.S. patent application Ser. No. 11/743,104, assigned to the Applicant of the present disclosure, in an Assignment, recorded on Oct. 10, 2007, at Reel 019942, Frame 0565.

Furthermore, a detection and identification transponder according to some embodiments may include more than one identification and/or presence/absence transponders. In these embodiments each identification transponder may include a distinct identifier. Furthermore, in any of the embodiments, each identification transponder may include more than one identifier. In addition, although particular uses of some embodiments of a detection and identification transponder have been described for a thorough understanding of the embodiments, other uses are contemplated to be within the scope of the present disclosure and the claims that follow. For example, the detection and identification transponder can be used to ensure presence of necessary objects before surgery and/or inventorying their attributes, such as a life-cycle attribute, maintenance schedule attribute, identification attribute, and/or use history attribute.

The various embodiments described above can be combined to provide further embodiments. All of the U.S. patents, U.S. patent application publications, U.S. Provisional Patent Application Ser. No. 61/056,229, filed May 27, 2008; U.S. Provisional Patent Application Ser. No. 61/102,749, filed Oct. 3, 2008, U.S. patent application Ser. No. 11/743,104, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system for detecting and identifying an object, the system comprising:
   an identification transponder including at least a first inductive winding and an integrated circuit that stores an identifier, the first inductive winding electrically coupled to the integrated circuit and operable to transmit an identification signal from the identification transponder in response to receipt of an interrogation signal in a first frequency range, the identification signal encoding an identifier stored by the integrated circuit;
   a presence/absence transponder including a resonant inductive/capacitive tank circuit having at least a second inductive winding and a capacitor, the second inductive winding electrically coupled to the capacitor and operable to transmit a presence/absence signal from the presence/absence transponder in response to an interrogation signal in a second frequency range, the presence/absence response signal omitting any unique identifying information, the presence/absence transponder physically coupled to the identification transponder to form an integral detection and identification transponder that can selectively be attached to the object;

wherein the first inductive winding includes a first core portion and a first conductive wire wound about the first core portion and the second inductive winding includes a second core portion and a second conductive wire wound about the second core portion; and a coupling member configured to attach the integral detection and identification transponder to the object without impeding performance of the object wherein at least one of the first core portion or the second core portion includes a hollow space, the coupling member extending from the hollow space.

2. The system of claim 1 wherein the coupling member further physically couples the presence/absence transponder to the identification transponder.

3. The system of claim 1 wherein the first core portion is coupled to the second core portion, and the first core portion and the second core portion are made from a ferrite material.

4. The system of claim 1 wherein the first core portion and the second core portion are formed from a unitary body of ferrite material.

5. The system of claim 1 wherein the first core portion includes a first end portion having a first recess sized and dimensioned to receive a first electrical or electronic component.

6. The system of claim 5 wherein the first core portion includes a first perimeter having a first pair of slots that communicate with the first recess, the slots of the first pair of slots sized and dimensioned to receive a portion of a respective wire therein.

7. The system of claim 5 wherein the second core portion includes a second end portion having a pair of through-holes sized and dimensioned to receive a portion of a respective wire therethrough.

8. The system of claim 5 wherein the second core portion includes a second end portion having a second recess sized and dimensioned to receive a second electrical or electronic component.

9. The system of claim 8 wherein the second core portion includes a second perimeter having a second pair of slots that communicate with the second recess, the slots of the second pair of slots sized and dimensioned to receive a portion of a respective wire therein.

10. The system of claim 9 wherein a wall portion is located between the first and the second end portions, the wall portion electrically insulating the first and the second inductive windings from each other.

11. The system of claim 1 wherein the first core portion and the second core portion form a common core and at least a portion of the first conductive wire is interlaced with at least a portion of the second conductive wire around the common core.

12. A system for detecting and identifying an object, the system comprising:

an identification transponding means for transmitting an identification signal in response to a first interrogation signal, the identification signal including identification information that uniquely identifies the identification transponding means;

a presence/absence transponding means for transmitting a presence/absence signal in response to a second interrogation signal, the presence/absence signal excluding identification information that uniquely identifies the presence/absence transponder, the second interrogation signal different from the first interrogation signal, wherein the identification transponding means and the presence/absence transponding means are physically coupled to one another to form an integral detection and identification transponder configured to be selectively attached to the object;

wherein the identification transponding means includes an integrated circuit and a first antenna coupled to the integrated circuit and the presence/absence transponding means includes a capacitor and a second antenna coupled to the capacitor; and a conductive core having a first portion and a second portion wherein the first antenna includes a conductive wire wound about the first portion of the conductive core, and the second antenna includes a conductive wire wound about the second portion of the conductive core.

13. The system of claim 12 wherein the conductive core is made from a ferrite rod and includes a first end and a second end, the integrated circuit coupled to the conductive core toward the first end, and the capacitor coupled to the conductive core toward the second end.

14. The system of claim 12 wherein the first antenna includes a first core and a first inductive winding wound about the first core, and the second antenna includes a second core and a second inductive winding wound about the second core.

15. The system of claim 14 wherein the first core includes an outer wall, an inner wall, and an elongated portion extending between the outer wall and the inner wall, the first inductive winding wound about the intermediate portion of the first core, and the second core includes an outer wall, an inner wall, and an elongated portion extending between the outer wall and the inner wall, the second inductive winding wound about the intermediate portion of the second core, the inner wall of the first core coupled to the inner wall of the second core.

16. The system of claim 15, further comprising:

a physical coupling member coupling the respective inner walls of the first core and the second core, the physical coupling member configured to couple the integral detection and identification transponder to the object.

17. The system of claim 14 wherein the second core includes a hollow space configured to insertably secure at least a portion of the identification transponding means.

* * * * *